(12) United States Patent
Villegas et al.

(10) Patent No.: US 9,440,023 B2
(45) Date of Patent: *Sep. 13, 2016

(54) DRUG DELIVERY SAFETY SYSTEM

(71) Applicant: ALFRED E. MANN FOUNDATION FOR SCIENTIFIC RESEARCH, Santa Clarita, CA (US)

(72) Inventors: Daniel Hernandez Villegas, Porter Ranch, CA (US); Brian Michael Shelton, Altadena, CA (US); Scott Robert Gibson, Granada Hills, CA (US)

(73) Assignee: MEDALLION THERAPEUTICS, INC., Santa Clarita, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 14/223,828

(22) Filed: Mar. 24, 2014

(65) Prior Publication Data

US 2014/0207122 A1 Jul. 24, 2014

Related U.S. Application Data

(63) Continuation of application No. 11/836,709, filed on Aug. 9, 2007, now Pat. No. 8,683,381.

(51) Int. Cl.
*G06F 3/048* (2013.01)
*A61M 5/142* (2006.01)
*G06F 19/00* (2011.01)

(52) U.S. Cl.
CPC ...... *A61M 5/14276* (2013.01); *G06F 19/3468* (2013.01); *A61M 5/14244* (2013.01); *A61M 2005/14208* (2013.01); *A61M 2205/3386* (2013.01); *A61M 2205/3507* (2013.01); *A61M 2205/3523* (2013.01); *A61M 2205/3592* (2013.01); *A61M 2205/50* (2013.01); *A61M 2205/502* (2013.01); *A61M 2205/581* (2013.01)

(58) Field of Classification Search
CPC .................................................. G06F 19/3406
See application file for complete search history.

(56) References Cited

U.S. PATENT DOCUMENTS

| | | | |
|---|---|---|---|
| 6,269,340 B1 | 7/2001 | Ford et al. | |
| 6,381,496 B1 | 4/2002 | Meadows et al. | |
| 6,694,334 B2 | 2/2004 | DuLong et al. | |
| 6,796,956 B2* | 9/2004 | Hartlaub | A61M 5/14276 604/65 |
| 6,880,564 B2 | 4/2005 | Erickson | |
| 6,957,655 B2 | 10/2005 | Erickson et al. | |
| 7,043,305 B2 | 5/2006 | KenKnight et al. | |
| 7,054,782 B2 | 5/2006 | Hartlaub | |
| 7,072,725 B2* | 7/2006 | Bristol | G06Q 50/22 604/65 |
| 7,471,994 B2* | 12/2008 | Ford | A61M 5/172 604/151 |
| 7,551,078 B2* | 6/2009 | Carlson | A61B 5/0002 128/903 |
| 7,945,452 B2* | 5/2011 | Fathallah | G06F 19/3406 705/2 |
| 8,149,131 B2* | 4/2012 | Blomquist | G06F 19/326 128/897 |
| 8,435,206 B2* | 5/2013 | Evans | A61M 5/172 604/19 |

(Continued)

Primary Examiner — Ryan Pitaro
(74) Attorney, Agent, or Firm — Henricks, Slavin & Holmes LLP

(57) ABSTRACT

A drug delivery safety system includes a programmer with a display and a communications device adapted to communicate with an ambulatory medical device. The programmer has access to a database of information, and is adapted to receive and process the information and a user input and to control the display to provide a graphical user interface that prompts a user of the programmer to provide an additional user input when the user input requests a drug delivery protocol for the ambulatory medical device that is not already stored in the database as a clinician-approved drug delivery protocol.

42 Claims, 16 Drawing Sheets

(56) References Cited

U.S. PATENT DOCUMENTS

| | | | |
|---|---|---|---|
| 8,683,381 B2 | 3/2014 | Villegas et al. | |
| 2001/0049673 A1 | 12/2001 | Dulong et al. | |
| 2001/0056358 A1 | 12/2001 | Dulong et al. | |
| 2002/0138155 A1 | 9/2002 | Bristol | |
| 2002/0143580 A1* | 10/2002 | Bristol | G06Q 50/22 705/2 |
| 2002/0193679 A1* | 12/2002 | Malave | A61M 5/172 600/407 |
| 2003/0163088 A1* | 8/2003 | Blomquist | G06F 19/3412 604/131 |
| 2003/0163789 A1* | 8/2003 | Blomquist | A61M 5/142 715/234 |
| 2004/0049245 A1 | 3/2004 | Gass | |
| 2004/0158193 A1* | 8/2004 | Bui | A61M 5/172 604/65 |
| 2004/0172301 A1* | 9/2004 | Mihai | A61B 5/0002 705/2 |
| 2004/0193090 A1* | 9/2004 | Lebel | A61N 1/37211 604/1 |
| 2005/0143864 A1* | 6/2005 | Blomquist | A61M 5/1452 700/282 |
| 2005/0154537 A1* | 7/2005 | Kutzko | A61K 49/0004 702/19 |
| 2005/0177096 A1* | 8/2005 | Bollish | A61B 5/02055 604/65 |
| 2006/0100907 A1* | 5/2006 | Holland | G06Q 50/24 705/3 |
| 2006/0129433 A1* | 6/2006 | Koneru | G06F 19/322 705/3 |
| 2006/0149416 A1* | 7/2006 | Mohapatra | G06F 19/322 700/242 |
| 2006/0173444 A1* | 8/2006 | Choy | A61N 1/37211 604/891.1 |
| 2006/0229551 A1* | 10/2006 | Martinez | A61M 5/172 604/67 |
| 2006/0229557 A1* | 10/2006 | Fathallah | G06F 19/3406 604/131 |
| 2006/0235472 A1 | 10/2006 | Goetz et al. | |
| 2006/0265140 A1 | 11/2006 | Hartlaub | |
| 2007/0118405 A1* | 5/2007 | Campbell | A61B 5/14532 705/2 |
| 2008/0033402 A1 | 2/2008 | Blomquist | |
| 2009/0043291 A1* | 2/2009 | Thompson | A61B 5/4839 604/891.1 |
| 2009/0143580 A1 | 6/2009 | McArthur et al. | |
| 2012/0290041 A1* | 11/2012 | Kim | A61N 1/36071 607/46 |

\* cited by examiner

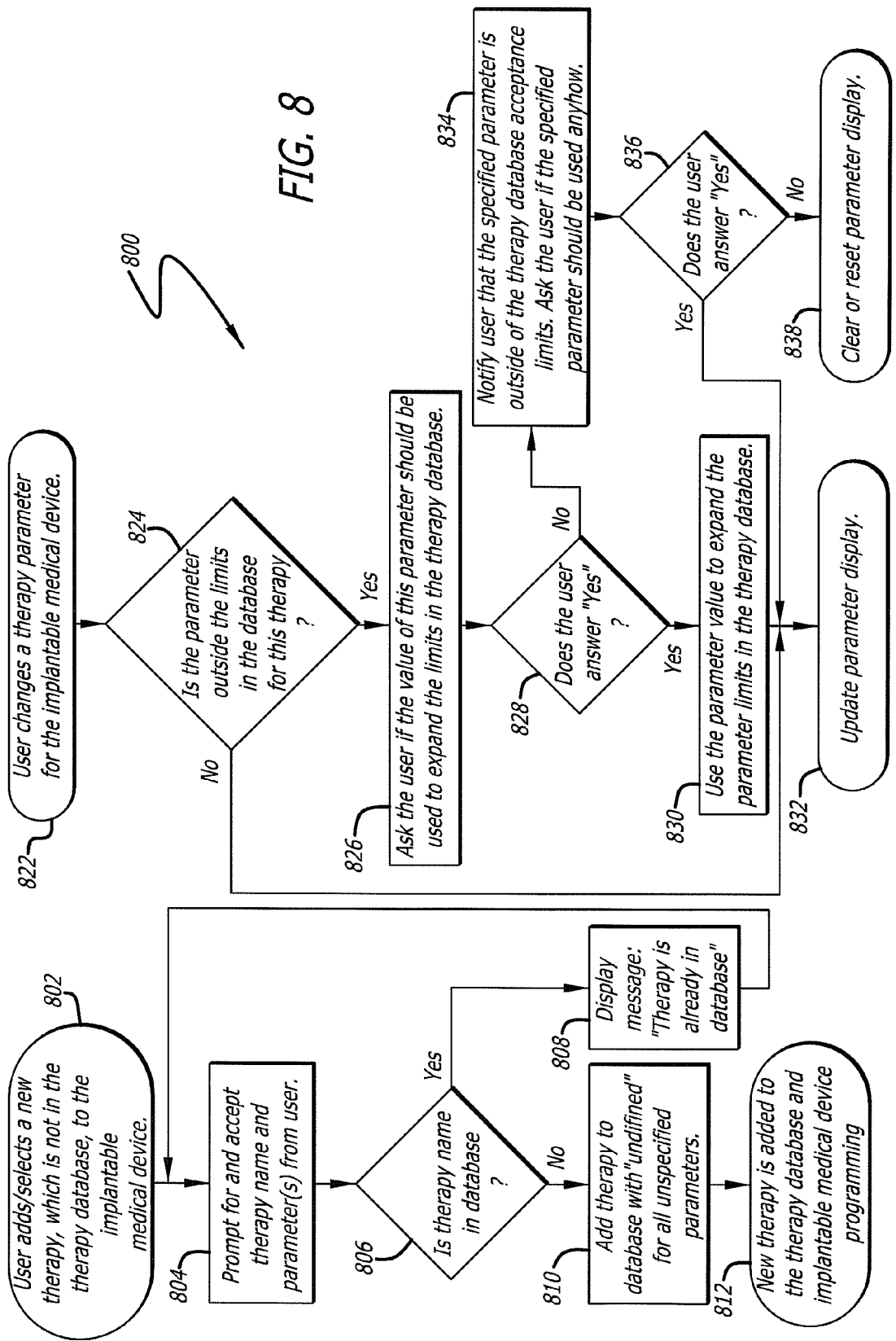

FIG. 12

| Medication | Display Units | Max. Base Rate | Rate Units | Max. Daily Dose | Dosage Units | Max. Concentration | Concentration Units | PCA Med. |
|---|---|---|---|---|---|---|---|---|
| Drug X | mg/mL | | 0.36 mL/hr | 10.0 | mg/day | 5.0 | mg/mL | No |
| Med Z | ug/mL | | 0.36 mL/hr | 20.0 | ug/day | 10.0 | ug/mL | Yes |
| Medication A | ug/mL | | | | | | | Yes |
| Medication B | mg/mL | | | | | | | No |
| Medication C | mg/mL | | | | | | | No |
| Medication D | ug/mL | | | | | | | No |
| Medication E | mg/mL | | 0.001 mL/hr | 1.0 | mg/day | 1.0 | mg/mL | No |
| Medication F | % | | 0.36 mL/hr | 3.0 | mg/day | 5.0 | % | Yes |
| Morphine | mg/mL | | | | | | | No |
| Saline | ug/mL | | | | | | | No |
| Test Med | ug/mL | | | | | | | |

DRUG DELIVERY SAFETY SYSTEM

CROSS-REFERENCE TO RELATED APPLICATIONS

This application is a continuation of U.S. Utility patent application Ser. No. 11/836,709, entitled "Drug Delivery Safety System", filed on Aug. 9, 2007 (now U.S. Pat. No. 8,683,381, issued on Mar. 25, 2014), which is hereby incorporated by reference.

BACKGROUND OF THE INVENTIONS

1. Field of Inventions

The present inventions relate generally to systems for delivering drugs to ambulatory medical devices such as implantable drug pumps (IDPs).

2. Description of the Related Art

Known implantable drug pumps can be used to deliver several different types of drugs (e.g., to treat various types of pain and spasticity), with rates of delivery and units of these rates that often vary widely. Implantable drug pumps, especially for intrathecal delivery, can be used to deliver a diverse array of drugs of differing concentrations, which makes it difficult to put bounds on the allowable delivery rates. For example, because any one of a number of drugs of various concentrations can be used, it is problematic to limit the overall rate of the pump.

It would be helpful to be able to provide a drug delivery safety system that allows a programmer to put bounds on the allowable delivery rates for each drug. It would also be useful to be able to provide a drug delivery safety system that allows a programmer of an implantable drug pump to check a specified delivery rate to verify that it is within a safe limit. Additionally, it would be helpful to be able to provide safety features to implantable medical device programmers in order to limit the possibility that a clinician would program a harmful or uncomfortable therapeutic regimen.

SUMMARY OF THE INVENTIONS

In an example embodiment, a drug delivery safety system includes a programmer with a display and a communications device adapted to communicate with an ambulatory medical device. The programmer has access to a database of information, and is adapted to receive and process the information and a user input and to control the display to provide a graphical user interface that prompts a user of the programmer to provide an additional user input when the user input requests a drug delivery protocol for the ambulatory medical device that is not already stored in the database as a clinician-approved drug delivery protocol.

In an example embodiment, a drug delivery safety system includes a programmer with a display and a communications device adapted to communicate with an implantable drug pump. The programmer has access to a database of therapeutic limits information relating to the implantable drug pump, and is adapted to receive and process the therapeutic limits information and a user input relating to a requested change to a drug delivery protocol currently associated with the implantable drug pump, and to control the display to provide an indication of an estimated date in which the implantable drug pump will experience a low reservoir condition.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIG. 8 is a flow chart in accordance with an embodiment of the present invention where a user changes a therapy parameter for an implantable medical device.

FIG. 12 shows a graphical user interface (displaying a clinic formulary) generated by a pump programmer according to an example embodiment of the present invention.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present remote controls or programmers have application in a wide variety of medical device systems. One example of such a system is an implantable infusion device system and the present inventions are discussed in the context of implantable infusion device systems. The present inventions are not, however, limited to implantable infusion device systems and are instead also applicable to other medical device systems that currently exist, or are yet to be developed. For example, the present inventions are applicable to other ambulatory medical device systems. Such systems include, but are not limited to, externally carried infusion pump systems, implantable pacemaker and/or defibrillator systems, implantable neural stimulator systems, and implantable and/or externally carried physiologic sensor systems.

Figure 1:
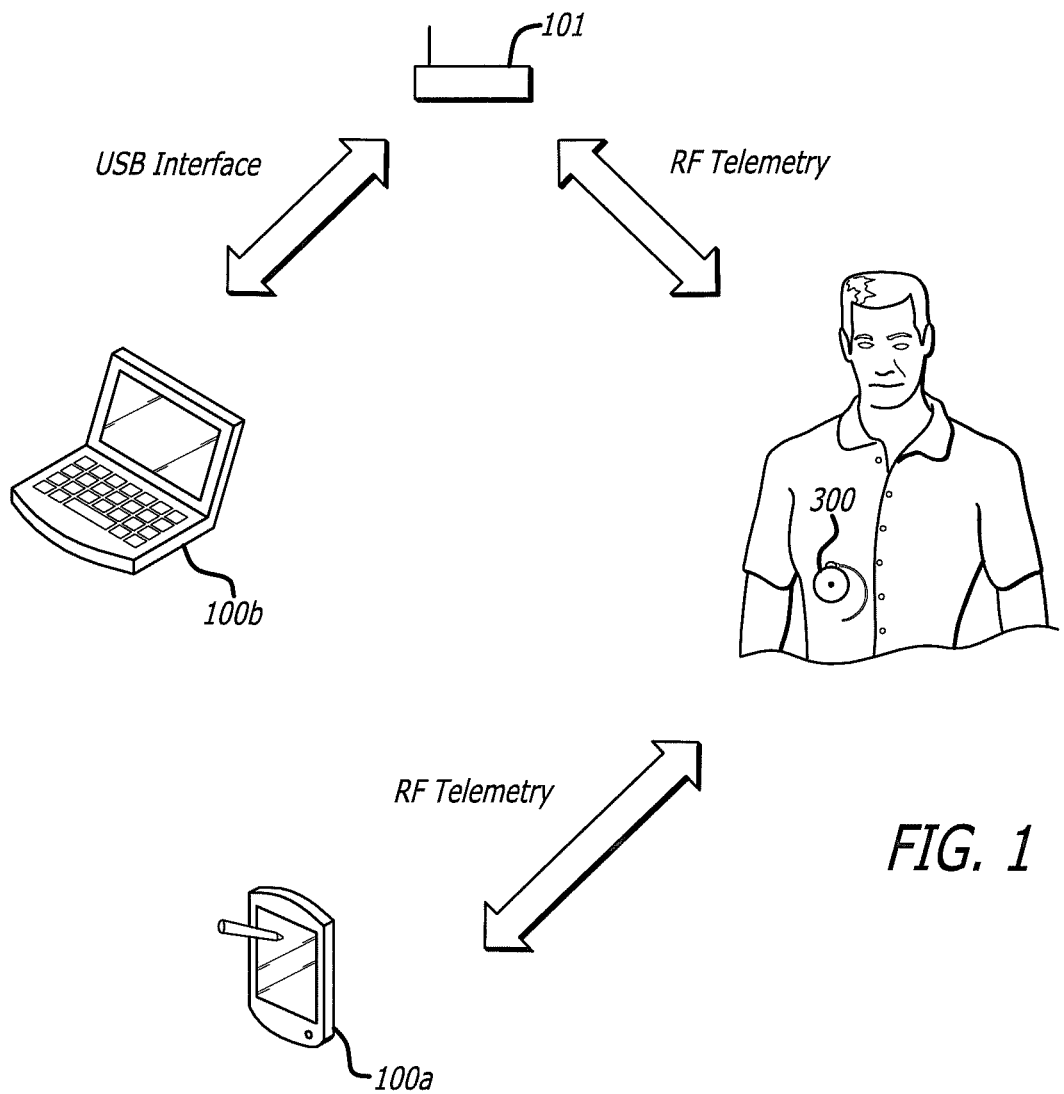
FIG. 1 illustrates an implantable medical device and example programmers/controllers, which embody the drug delivery safety systems described herein.

One example of a programmer in accordance with the present inventions is an implantable infusion device system. The implantable infusion device system may include any one of the remote controls or programmers described herein in combination with an implantable infusion device. FIG. 1 illustrates an implantable medical device 300 and example programmers/controllers, which embody the drug delivery safety systems described herein. The example programmers/controllers includes a programmer 100a (such as a portable computing device (PCD) or personal digital assistant (PDA)) and a clinician programmer 100b (such as a clinician programmer/field support system). In this example, the programmer 100a includes a communication device which facilitates radio frequency (RF) communications with the implantable medical device 300 so that RF telemetry can be communicated between the devices. Also in this example, the clinician programmer 100b is connected to a programmer interface module 101 with a USB Interface; the programmer interface module 101, in turn, facilitates RF communications between the clinician programmer 100b and the implantable medical device 300. It should be understood that other types of programmers/controllers as well as other communications interfaces can also be employed.

Figure 2:
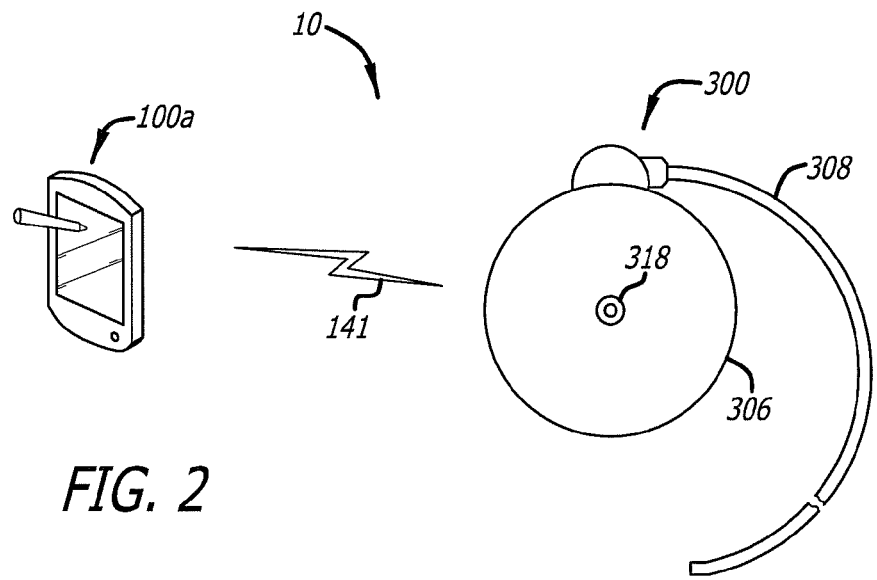
FIG. 2 is a plan view of a programmer in accordance with one embodiment of the present invention, shown establishing a communications link with an implantable medical device.

Referring to FIG. 2, in an example embodiment, an implantable medical device system 10 includes a programmer 100a and an implantable medical device 300. In an example embodiment, the programmer 100a includes a battery or other power source 136, a controller 138, such as a microprocessor, microcontroller or other control circuitry, memory 139, a user input mechanism 142 (such as a keyboard, mouse, touch screen and/or voice recognition device), one or more LEDs 146 (and/or alarm 147), and a display 148. The memory 139 can also be contained within the controller 138 (e.g., within a microcontroller). By way of example and not of limitation, the alarm 147 can include one or more of an audio speaker and a vibration device. A communication device 140 (including an antenna if necessary) is also provided. In an example embodiment, the display 148 is a touch screen configured to receive user inputs, i.e., at least a portion of the functionality of the user input mechanism 142 is provided by the display 148.

The communication device 140 establishes a communications link 141 (e.g., an RF communications link) with the implantable medical device 300. Although the present inventions are not limited to any particular communication device, in an example embodiment, the communication device 140 is a telemetry device that transmits an RF signal at a specified frequency or set of frequencies. The RF signal may, in some instances, be a carrier signal that carries bit streams. The communication device 140 is also configured to receive signals from the implantable medical device 300. Other exemplary communication devices include oscillating magnetic field communication devices, static magnetic field communication devices, optical communication devices, ultrasound communication devices and direct electrical communication devices.

In this example embodiment, the implantable medical device 300 is an implantable infusion device and includes a medication reservoir 302 and a pump or other fluid transfer device 304 within a housing 306. The pump 304 transfers medication from the reservoir 302 through a catheter 308 to the target region within the body. Operation of the implantable medical device 300 is controlled by a controller 310, such as a microprocessor, microcontroller or other control circuitry, in accordance with instructions stored in memory 312. Power is provided by a battery or other power source 314. An alarm 316 (e.g., an audible alarm such as an audio speaker, and/or a vibration device) may also be provided in order to inform the patient, for example, when the amount of medication in the reservoir 302 is low or when the amount of energy stored in the battery 314 is low. A refill port 318, which allows the reservoir to be refilled while the implantable medical device 300 is within the patient, is positioned on the exterior of the housing 306.

A communication device 320 is also provided. In this example embodiment, the communication device 320 is configured to receive signals from, and transmit signals to, the programmer 100a. In an example embodiment, the communication device 320 is a telemetry device that transmits and receives RF signals at a specified frequency or set of frequencies. The RF (or other) signal may, in some instances, be a carrier signal that carries bit streams.

Figure 4:
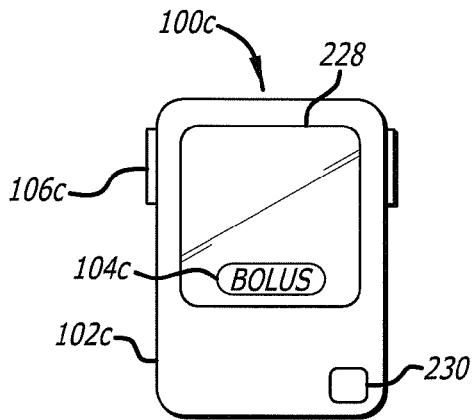
FIG. 4 is a plan view of a programmer in accordance with another embodiment of the present invention.

It should be noted here that, in the context of the present inventions, different types and/or combinations of user input devices can be employed with any given programmer/controller device. As illustrated for example in FIG. 4, the exemplary programmer 100c includes a housing 102c and a touch screen 228. A controller and a communication device (not shown) are also provided. The touch screen 228 may be used to display one or more button configurations in order to allow the user to accomplish various tasks. At least one of the displayed buttons is a bolus delivery button 104c. The housing 102c may also be provided with one or more button control elements 106c (e.g. buttons), which are operably connected to the controller, and a power on/off button 230.

Figure 5:
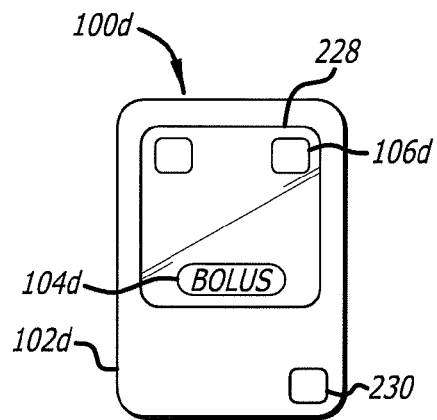
FIG. 5 is a plan view of a programmer in accordance with still another embodiment of the present invention.

One or more button control elements may, alternatively, be provided on a touch screen. Turning to FIG. 5, the exemplary programmer 100d includes a housing 102d, a touch screen 228 that may be used to, among other things, display a bolus delivery button 104d and a pair of button control elements 106d, and a power on/off button 230.

Figure 3:
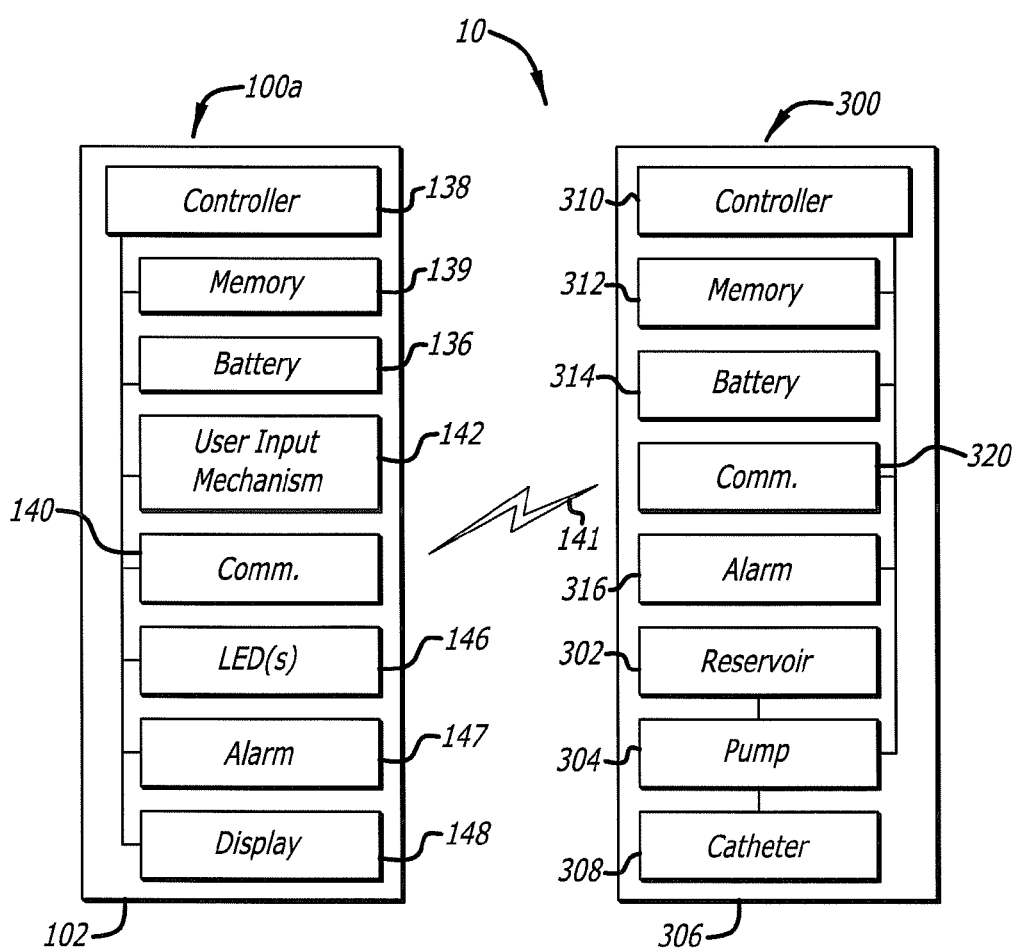
FIG. 3 is a block diagram of the programmer and implantable medical device of FIG. 2.

Referring again to FIG. 3, in this example embodiment, the controller 138 and memory 139 are contained within the housing 102 of the programmer 100a. The scope of the present invention also includes programmers or programming systems where the functionality of the controller 138, or a portion of this functionality, is "migrated" to a physical location that is external to the housing 102. Similarly, some or all of the memory 139 can be physically located external to the housing 102. Such external controller(s) and memory device(s) can be operatively interfaced with the programmer 100a with wireless or wired communication links.

In an example embodiment, a database of information relating to the implantable medical device 300 (e.g., an implantable drug pump) is stored in the memory 139. In an example embodiment, the information includes a list of clinician-approved drugs and dosage parameters such as rate, concentration, total daily dose, therapeutic limits, etc. associated with each of the drugs. In an example embodiment, a baseline database of information is initially uploaded into the memory 139. In an example embodiment, the controller 138 manages the function of uploading a database of information, as well as writing changes, additions or updates to the database of information. Under control of the controller 138 and in response to user inputs provided via the user input mechanism 142, the programmer 100a performs the various functions described herein, in particular, providing an interactive user interface, e.g., a graphical user interface (GUI), at the display 148.

Figure 6:
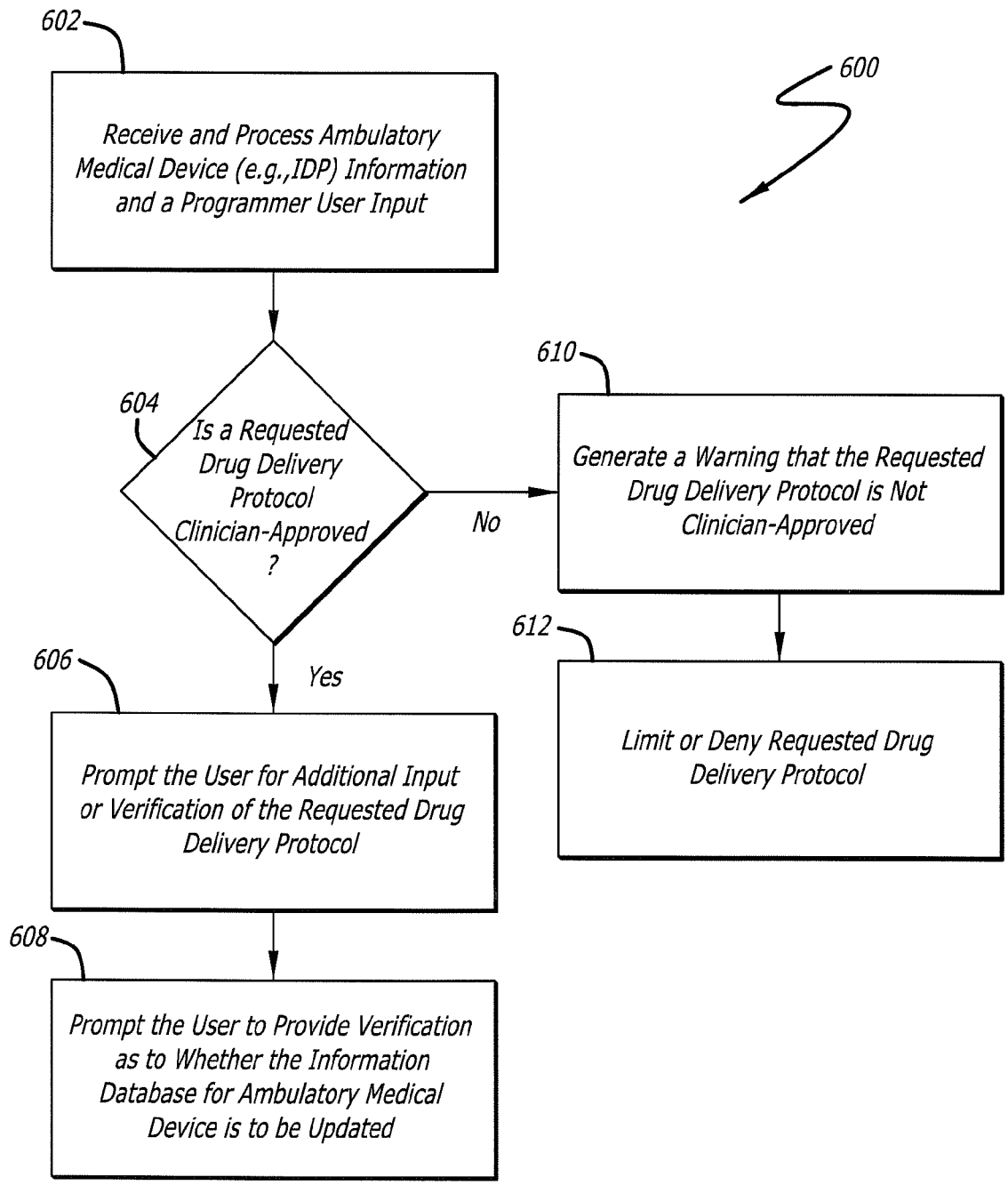
FIG. 6 is a flow chart in accordance with one embodiment of the present invention.

Referring to FIG. 6, in an example embodiment, a method 600 of controlling a drug delivery safety system is now described. At 602, ambulatory medical device (e.g., IDP) information and programmer user input(s) are received and processed by the controller 138. For example, a drug delivery protocol requested by a user of the programmer 100a is evaluated in relation to clinician-approved drug delivery protocols stored in database of information. At 604, it is determine whether a requested drug delivery protocol is clinician-approved. If the result of this determination is affirmative, the user of the programmer 100a, at 606, is prompted to provide an additional input or verification of the requested drug delivery protocol. At 608, the user is prompted to provide verification as to whether the database of information for the ambulatory medical device is to be updated. However, if the requested drug delivery protocol is not clinician-approved (vis-a-vis the database of information), at 610, the programmer 100a generates a warning indicating this. By way of example, the warning can be generated using one or more of the LED(s) 146, alarm 147, and display 148. At 612, the requested drug delivery protocol is limited or denied.

In example embodiments of drug delivery safety systems, the programmer 100a tracks a standard maximum dosage used for each drug that a clinician specifies on the programmer. If at any time, the clinician specifies a dosage that is greater than the standard maximum dosage, the programmer 100a alerts the clinician of the abnormally high rate. The programmer 100a then generates a user prompt, e.g., at the display 148, asking the clinician if this is an acceptable rate. If the clinician specifies "yes", then the programmer generates a prompt asking the clinician if this rate should be saved as the new standard maximum dosage. If the clinician specifies "yes", then the programmer 100a saves this rate in its database of standard maximum dosages and will associate this rate with the specified drug.

Figure 11:
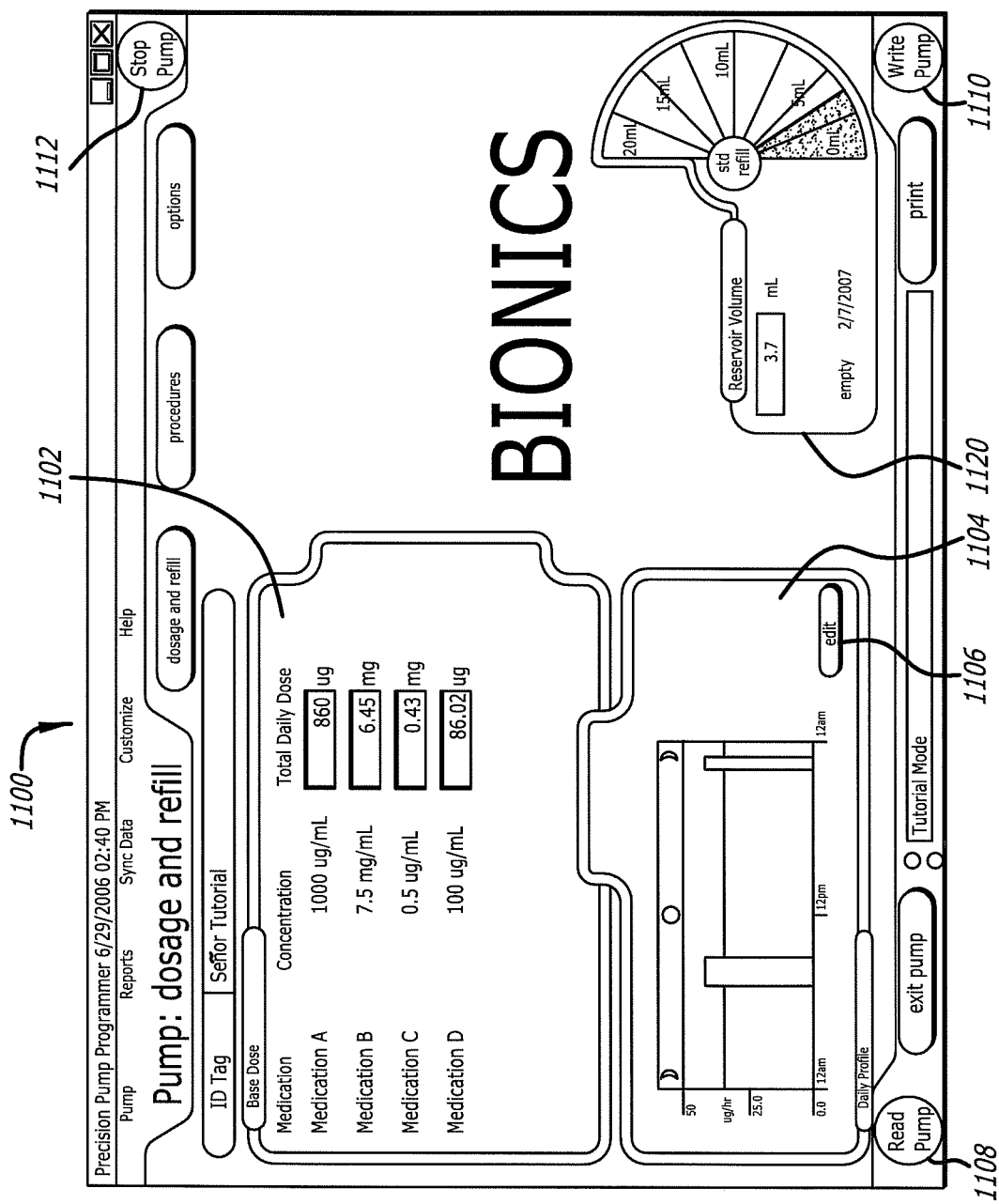
FIG. 11 shows a graphical user interface generated (displaying dosage and refill user interfaces) generated by a pump programmer according to an example embodiment of the present invention.

Example embodiments of drug delivery safety systems allow the user to edit or reset the rates for all (or some) of the drugs in its database. Referring to FIG. 11, in an example embodiment, a graphical user interface 1100 is generated at the display 148. In this example embodiment, the graphical user interface 1100, denoted "Pump: dosage and refill", includes a Base Dose display area 1102, which displays a table of information for Base Dose medications. More specifically, in this example embodiment, Base Dose display area 1102 shows a table of information organized under the headings: Medication, Concentration, and Total Daily Dose. In this example embodiment, the graphical user interface 1100 also includes a Daily Profile display area 1104 in which a daily profile for one or more drugs is shown, with drug(s) concentration plotted over time. This graphical presentation of the daily profile provides the clinician or other user of the programmer 100a with tool for assessing possible adjustments to the daily profile.

In an example embodiment, the programmer 100a is configured to generate the graphical user interface 1100 such that the Total Daily Dose (for each Medication) shown in the Base Dose display area 1102 can be adjusted by entering new dosages. In another example embodiment, the plot generated in the Daily Profile display area 1104 is automatically adjusted depending upon the dosages entered into the fields in the Total Daily Dose column. In an example embodiment, an edit button 1106 in the Daily Profile display area 1104, when actuated, permits a user to edit the daily profile. In another example embodiment, the Total Daily Dose value for each Medication is automatically adjusted depending upon changes made to the daily profile.

In this example embodiment, the graphical user interface 1100 also includes a Read Pump button 1108, a Write Pump button 1110, and a Stop Pump button 1112, which initiate these respective functions when actuated.

In an example embodiment, FIG. 12 shows a graphical user interface 1200 (displaying a Clinic Formulary table 1202) generated by the programmer 100a. In this example embodiment, the Clinic Formulary table 1202 shows each Medication, e.g., previously used, clinician-approved medications, in the database of information. In an example embodiment, the Clinic Formulary includes a therapy and drug database. In this example embodiment, for each Medication which is part of a dosage protocol, the Clinic Formulary table 1202 indicates: Display Units, Max. Base Rate, Rate Units, Max. Daily Dose, Dosage Units, Max. Concentration, Concentration Units, and PCA Med. information.

In an example embodiment, the programmer 100a keeps track of all drugs that the clinician has used in the past. When the clinician wishes to refill a pump with a new drug or drug mixture, he or she is provided with a list of all previously-used drugs and with an option to use/specify a drug that is not on this list. In an example embodiment, the add button 1204 causes the programmer 100a to generate a user interface which facilitates this function.

In an example embodiment, when a new drug is to be specified, the programmer 100a allows the clinician to type in the name of this new drug. This name is (at least temporarily) saved in a database or list of drugs. In an example embodiment, the name of the new drug then appears in the list of drugs that are in the drug mixture with which the pump has been or is about to be refilled. At this point, in an example embodiment, no delivery rate or rate units are displayed for the new drug. In an example embodiment, the user is then prompted to enter this information. After having entered this information, in an example embodiment, the programmer 100a generates a prompt asking the clinician if this rate and units should be saved in the drug database as the new maximum rate and default display units for the specified drug. When this drug is selected to be added for any patient's pump, in an example embodiment, the programmer 100a notifies the clinician or other user if the rate is above the maximum rate in the database.

Example embodiments of drug delivery safety systems provide confirmation dialogs for unexpectedly high (or low) rates. This protects against data entry errors by the clinician or other user.

Figure 13:
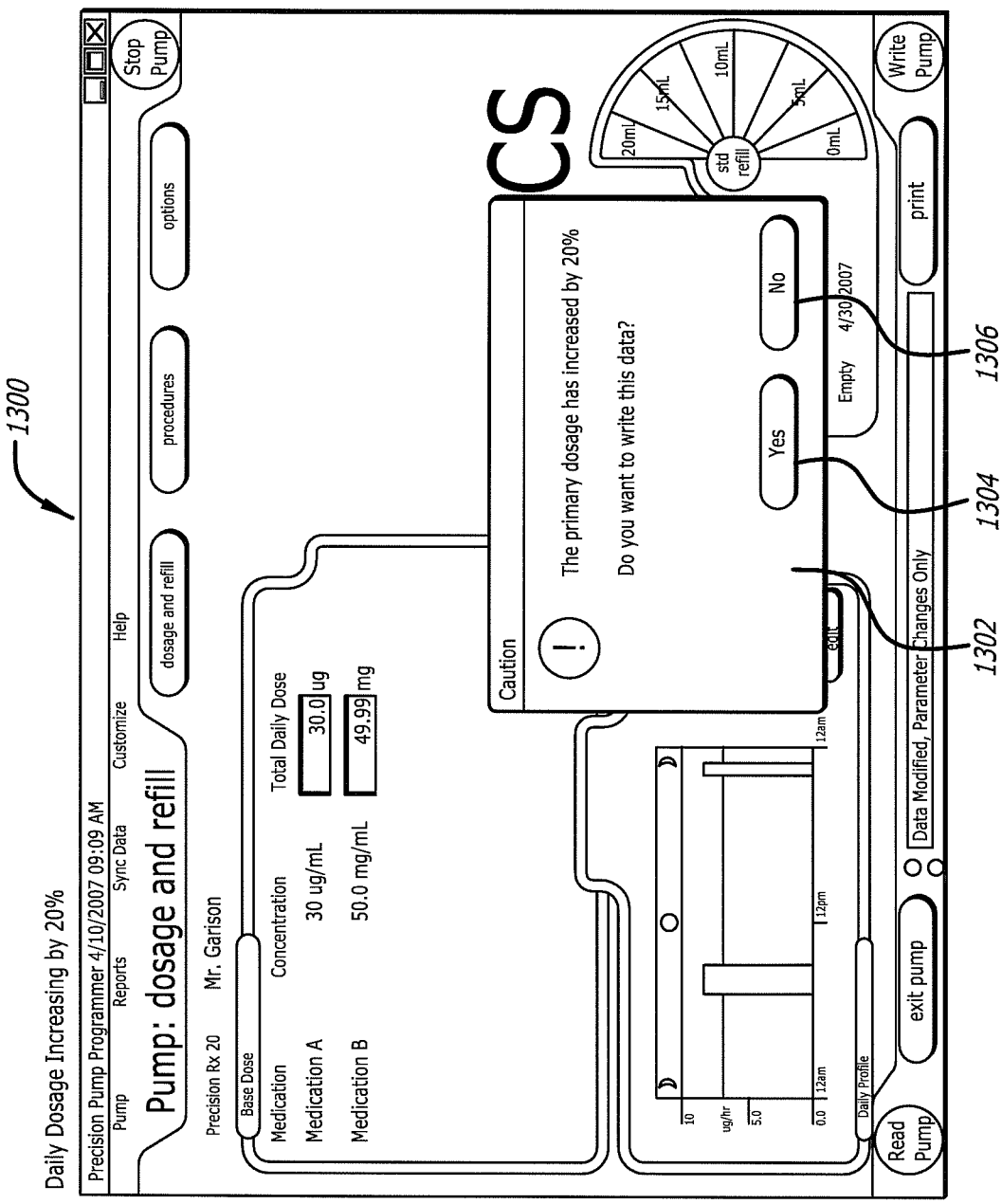
FIG. 13 shows a graphical user interface (indicating that a daily or primary dosage has increased by a threshold percentage) generated by a pump programmer according to an example embodiment of the present invention.
Figure 14:
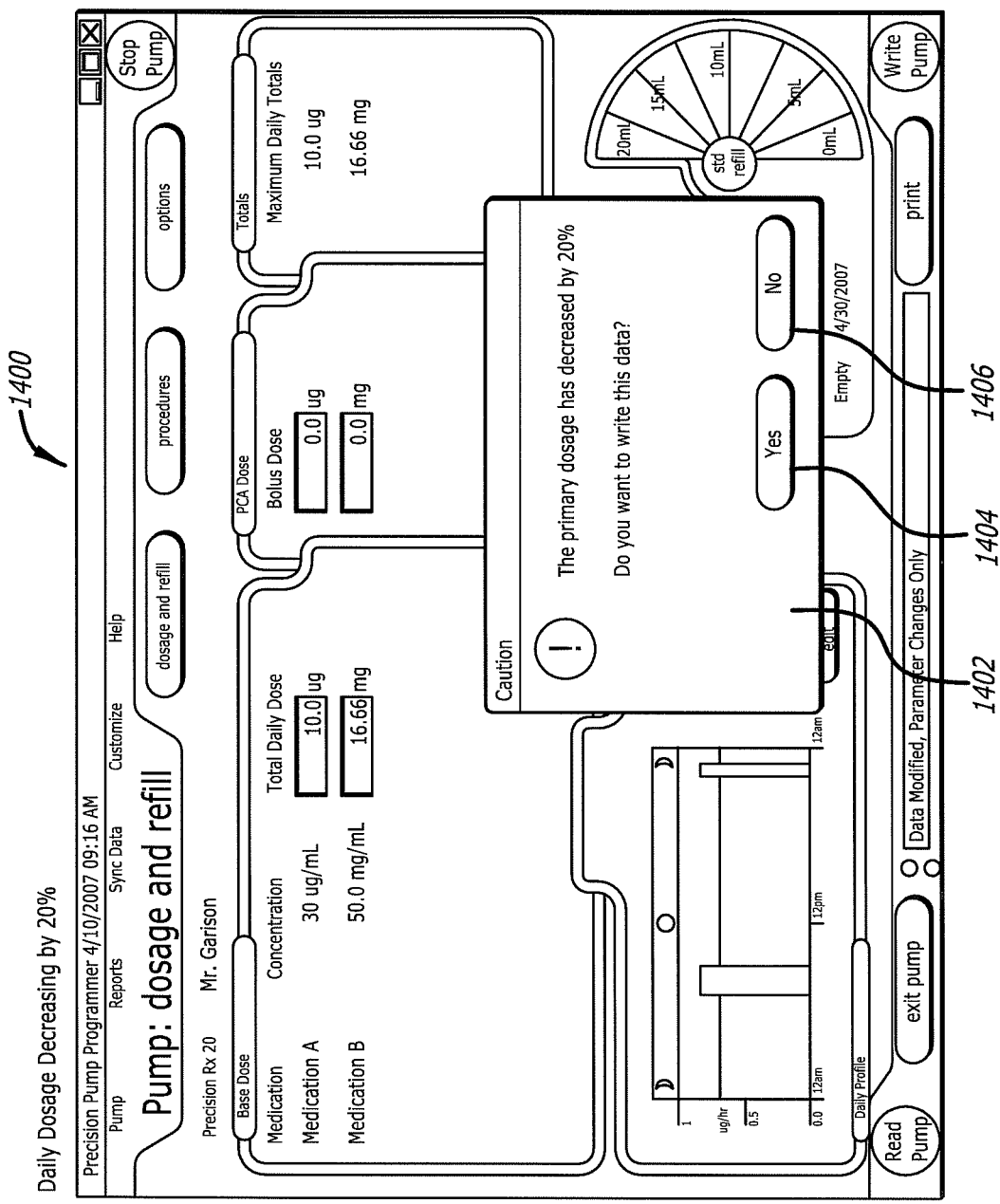
FIG. 14 shows a graphical user interface (indicating that a daily or primary dosage has decreased by a threshold percentage) generated by a pump programmer according to an example embodiment of the present invention.

FIG. 13 shows a graphical user interface 1300, with a "pop-up" window 1302 indicating that a daily or primary dosage has increased by a threshold percentage (in this example, by 20%). In this example embodiment, the "pop-up" window 1302 includes fields 1304 and 1306 which, when actuated (e.g., by positioning a cursor over the field and clicking a mouse), confirm or cancel a user's request for a particular dosage, respectively. Similarly, FIG. 14 shows a graphical user interface 1400, with a "pop-up" window 1402 indicating that a daily or primary dosage has decreased by a threshold percentage (in this example, by 20%). In this example embodiment, the "pop-up" window 1402 includes fields 1404 and 1406 which, when actuated (e.g., by positioning a cursor over the field and clicking a mouse), confirm or cancel a user's request for a particular dosage, respectively.

Example embodiments of drug delivery safety systems provide confirmation dialogs relating to requested PCA dosages. In an example embodiment, users are not allowed to enable PCA when at least one of the medications in the IDP's admixture has been defined not to be suitable for PCA in the Clinical Formulary. In an example embodiment, users cannot configure a PCA Bolus rate which exceeds a threshold rate, for example, 30 μL/minute (thirty microliters).

Figure 15:
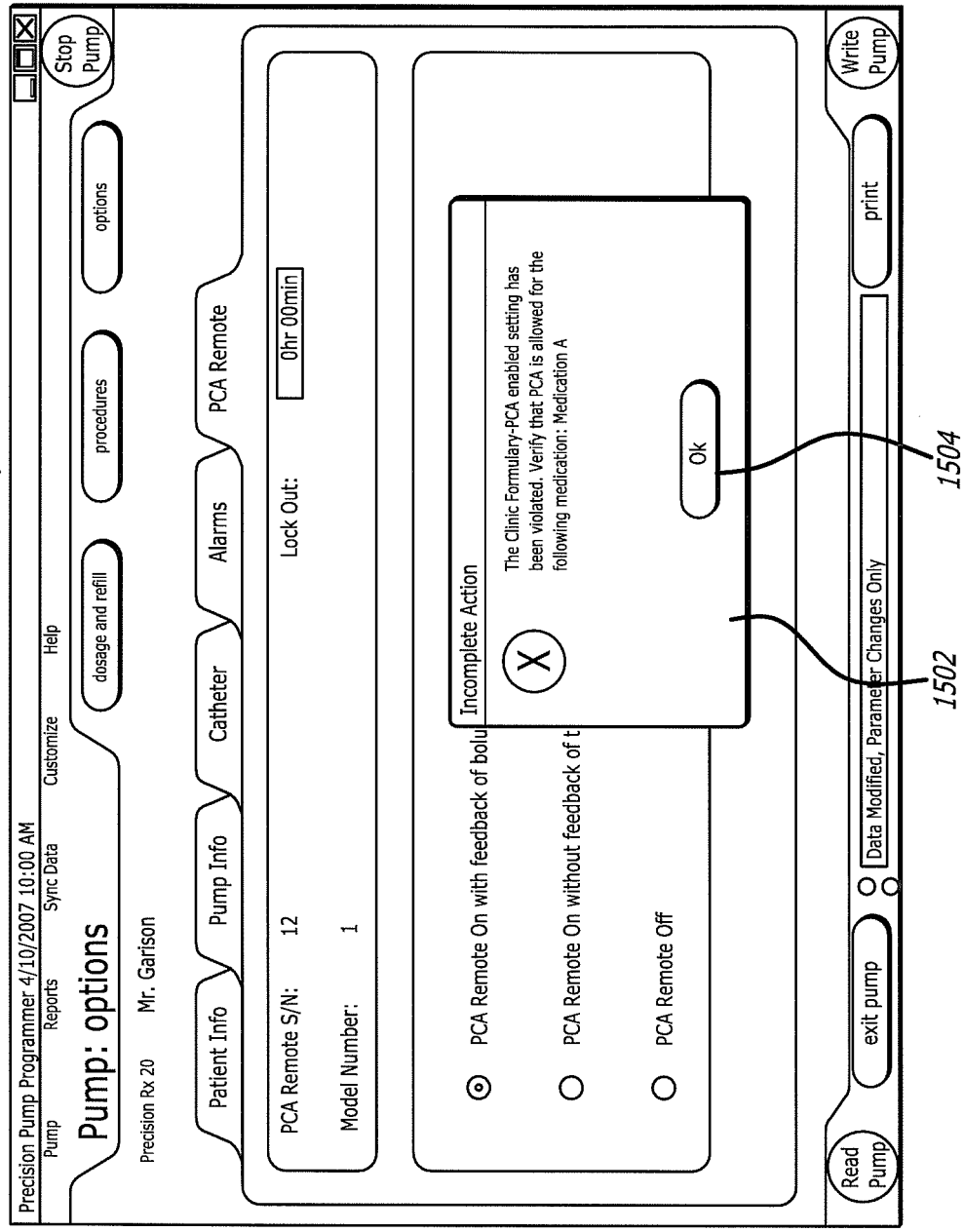
FIG. 15 shows a graphical user interface generated (indicating that, in an attempt to enable a Patient Controlled Analgesia (PCA) dosage, the medication has been defined not to be suitable for PCA in the Clinical Formulary) by a pump programmer according to an example embodiment of the present invention.

FIG. 15 shows a graphical user interface 1500, with a "pop-up" window 1502 indicating that, in an attempt to enable a PCA dosage, the medication has been defined not to be suitable for PCA in the Clinical Formulary. In this example embodiment, the "pop-up" window 1502 includes a field 1504 which, when actuated (e.g., by positioning a cursor over the field and clicking a mouse), verifies that PCA is allowed for the requested medication.

Figure 16:
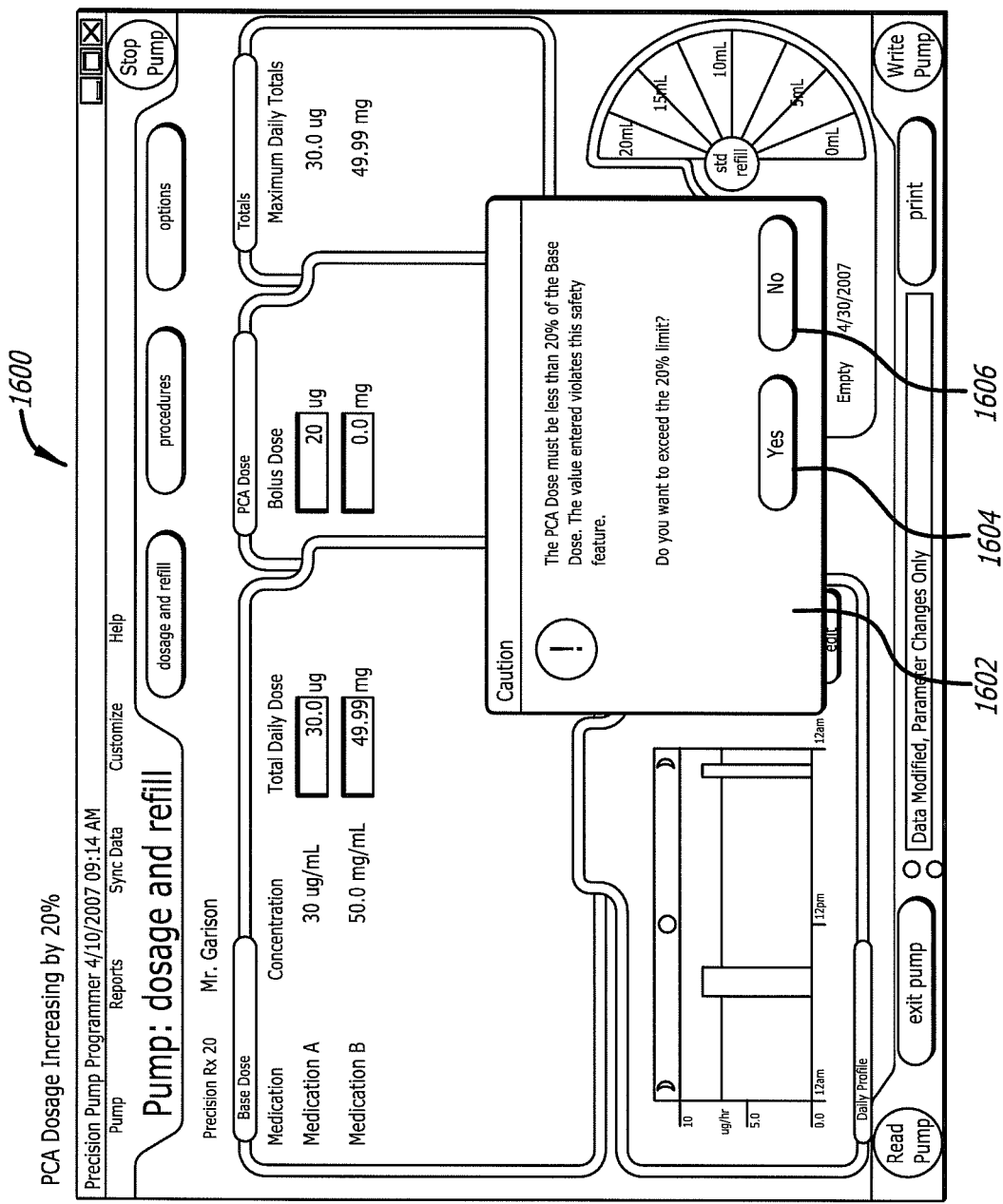
FIG. 16 shows a graphical user interface (indicating that a PCA dosage has increased by a threshold percentage) generated by a pump programmer according to an example embodiment of the present invention.
Figure 17:
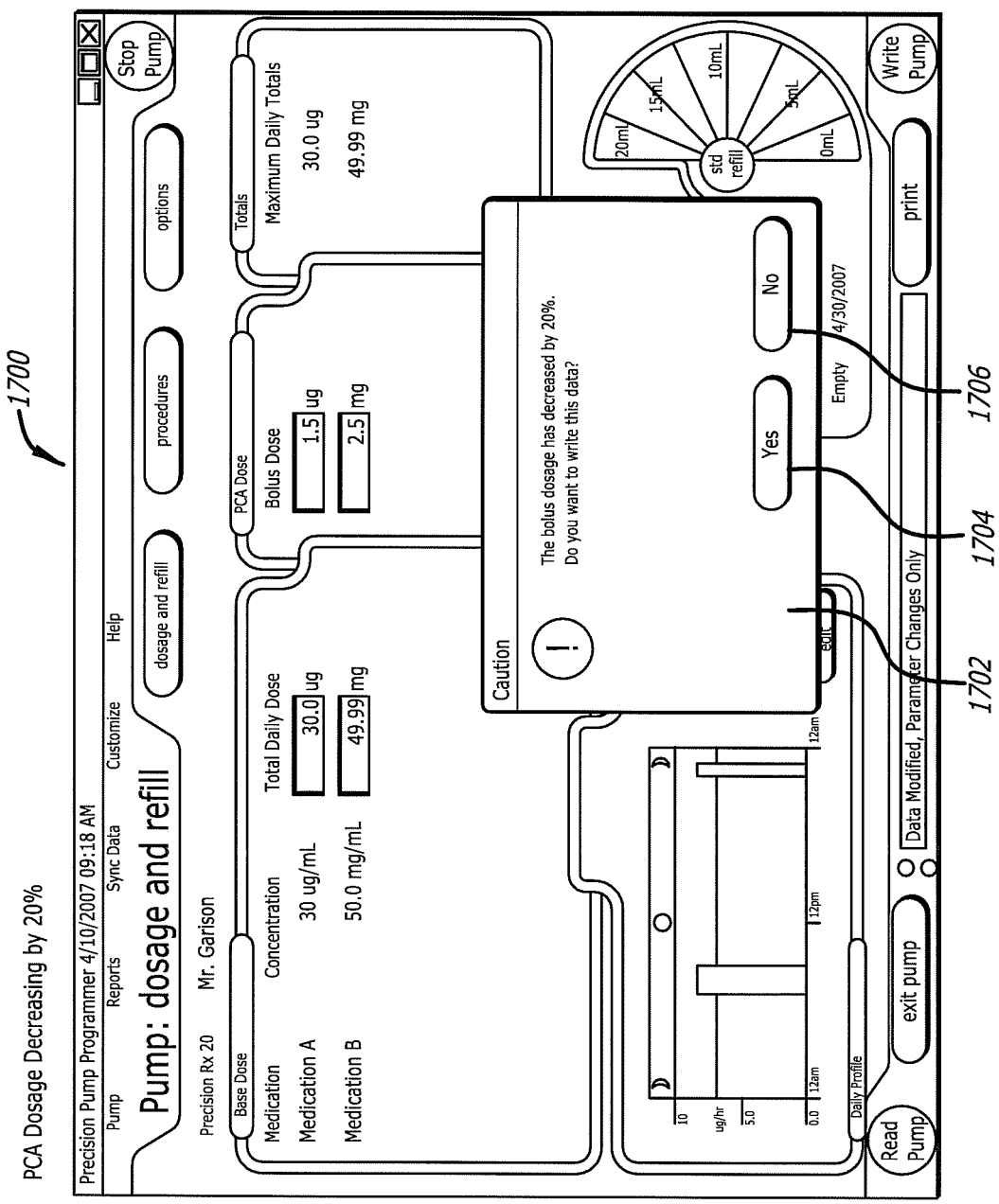
FIG. 17 shows a graphical user interface (indicating that a PCA dosage has decreased by a threshold percentage) generated by a pump programmer according to an example embodiment of the present invention.

FIG. 16 shows a graphical user interface 1600, with a "pop-up" window 1602 indicating that a PCA dosage is not less than an allowed threshold percentage (in this example, 20% of the Base Dose). In this example embodiment, the "pop-up" window 1602 includes fields 1604 and 1606 which, when actuated (e.g., by positioning a cursor over the field and clicking a mouse), confirm or cancel a user's request for a particular PCA dosage, respectively. Similarly, FIG. 17 shows a graphical user interface 1700, with a "pop-up" window 1702 indicating that a PCA dosage has decreased by a threshold percentage (in this example, by 20%). In this example embodiment, the "pop-up" window 1702 includes fields 1704 and 1706 which, when actuated (e.g., by positioning a cursor over the field and clicking a mouse), confirm or cancel a user's request for a particular PCA dosage, respectively.

Example embodiments of drug delivery safety systems provide confirmation dialogs relating to the writing of data to the ambulatory medical device (e.g., IDP). In an example embodiment, when the user requests queued data to be written to the IDP, the programmer generates a confirmation window which displays the data that is to be written to the IDP.

Figure 19:
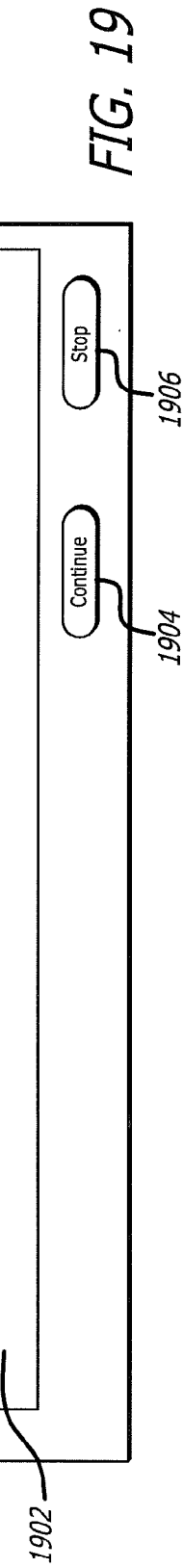
FIG. 19 shows a graphical user interface (presenting a write confirmation display) generated by a pump programmer according to an example embodiment of the present invention.

FIG. 19 shows a graphical user interface 1900, with a Write Confirmation Display window 1902 indicating both the previous and new programming values/information. In an example embodiment, all programming changes are highlighted (e.g., presented bold and/or in a different color). In an example embodiment, the Write Confirmation Display window 1902 reminds the user that a daily profile has not been configured, when this is the case (in this example, by displaying the text: "Pump Not Programmed"). In this example embodiment, the graphical user interface 1900 includes fields 1904 and 1906 which, when actuated (e.g., by positioning a cursor over the field and clicking a mouse), confirm or cancel a user's request to write new programming data, respectively.

Example embodiments of drug delivery safety systems are configured to track clinician-specified therapeutic parameters and to display warnings when abnormal parameters are specified. In an example embodiment, a programmer is configured (e.g., programmed) to track the drugs used for a particular disease type or disease state and uses this information to warn the clinician when an abnormal therapy is selected to treat a particular disease type or state. For an implantable drug pump, by way of example, the programmer displays a warning if a drug is used to treat a new disease type. For example, if Morphine Sulfate has only been used to treat nociceptive pain and Baclofen has only been used to treat spasticity, the programmer displays a warning if Morphine Sulfate is used to treat a patient with spasticity.

Example embodiments of drug delivery safety systems are configured to generate warnings or limitations for any therapeutic parameters by either tracking usage per clinic or per patient. For example, it is possible for a drug pump programmer to limit the medication delivery rate in response to the maximum rate previously used for the specified drug either within the clinic as a whole or for the specific patient being treated. Limiting or warning when clinic maximums for specified drugs are exceeded is appropriate, because drugs usually have side-effects that present themselves at dosages that are specific to drug type. Different patients can have different tolerances to any selected drug; therefore, displaying a warning based upon a patient-specific maximum rate for a drug is appropriate in some instances.

Example embodiments of drug delivery safety systems are configured to limit user input based upon therapy type. In an example embodiment, a drug delivery safety system is configured to update the acceptance limits for the critical therapy parameters by monitoring the clinician input.

Referring to FIG. 8, in an example embodiment, a method 800 of controlling a drug delivery safety system, in response to user changes to a therapy parameter for an implantable medical device, is now described. At 802, a user adds/selects a new therapy, which is not in the therapy database, to the implantable medical device. At 804, the user is prompted for the therapy name and parameter(s). A determination is made, at 806, as to whether the therapy name is in the database. If yes, at 808, a message is displayed, such as: "Therapy is already in database." If no, at 810, the therapy is added to the database with all unspecified parameters denoted as "undefined". At 812, the new therapy is added to the therapy database and to the implantable device programming.

At 822, a user changes a therapy parameter for the implantable medical device. A determination is made, at 824, as to whether the parameter is outside the limits in the database for this therapy. If no, there is no need to adjust parameter limits in the database and, at 832, the parameter display is updated. If yes, at 826, the user is prompted to indicate whether the value of this parameter should be used to expand the limits in the therapy database. At 828, the user answer to this prompt is processed. If the user answer is "Yes", at 830, the parameter value is used to expand the parameter limits in the therapy database. If the user answer is "No", at 834, the user is notified that the specified parameter is outside of the therapy database limits. Additionally, the user is asked to verify again that the specified parameter should be used. At 836, the user answer to this prompt is processed. If the user answer is "Yes", at 832, the parameter display is updated. If the user answer is "No", at 838, the parameter display is cleared or reset.

Example embodiments of drug delivery safety systems are configured to limit the concentration for specified drug(s) for an ambulatory medical device (e.g., an implantable pump system).

Figure 9:
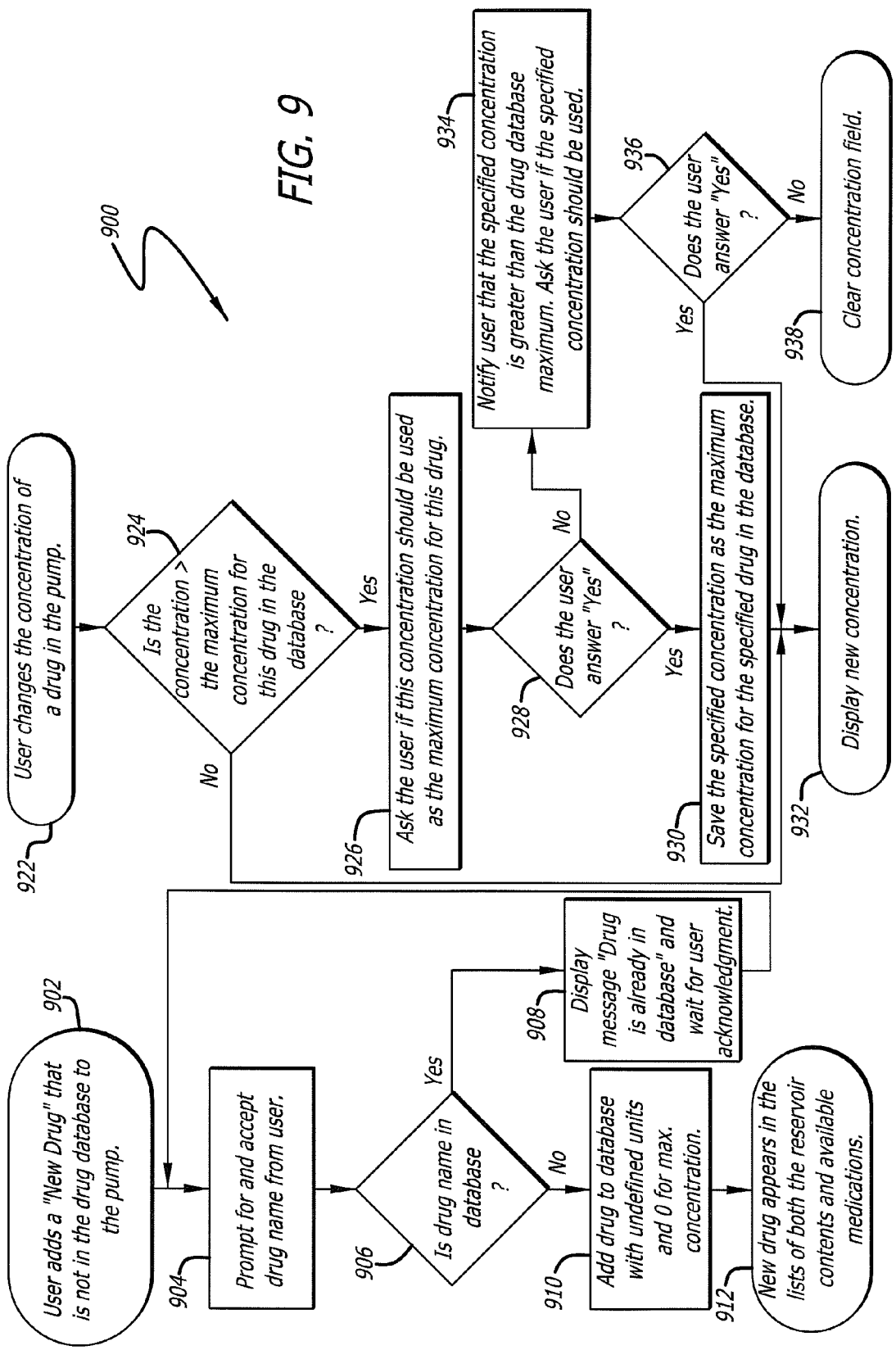
FIG. 9 is a flow chart in accordance with an embodiment of the present invention where a user changes the concentration of a drug in a pump.

Referring to FIG. 9, in an example embodiment, a method 900 of controlling a drug delivery safety system, in response to user changes to the concentration of a drug in a pump, is now described. At 902, a user adds a "New Drug" that is not in the drug database to the pump. At 904, the user is prompted for the drug name. A determination is made, at 906, as to whether the drug name is in the database. If yes, at 908, a message is displayed, such as: "Drug is already in database." If no, at 910, the drug is added to the database with undefined units and 0 for maximum concentration. At 912, the new drug appears in the lists for both the reservoir contents and available medications.

At 922, a user changes the concentration of a drug in the pump. A determination is made, at 924, as to whether the concentration is greater than the maximum concentration for this drug in the database. If no, there is no need to adjust the maximum concentration in the database and, at 932, the new concentration is displayed. If yes, at 926, the user is prompted to indicate whether this concentration should be used as the maximum concentration for this drug. At 928, the user answer to this prompt is processed. If the user answer is "Yes", at 930, the specified concentration is saved as the maximum concentration for the specified drug in the database. If the user answer is "No", at 934, the user is notified that the specified concentration is greater than the drug database maximum. Additionally, the user is asked to verify again that the specified concentration should be used. At 936, the user answer to this prompt is processed. If the user answer is "Yes", at 932, the new concentration is displayed. If the user answer is "No", at 938, the concentration field is cleared.

Example embodiments of drug delivery safety systems are configured to limit the programmed drug rate for an ambulatory medical device (e.g., an implantable pump system).

Figure 10:
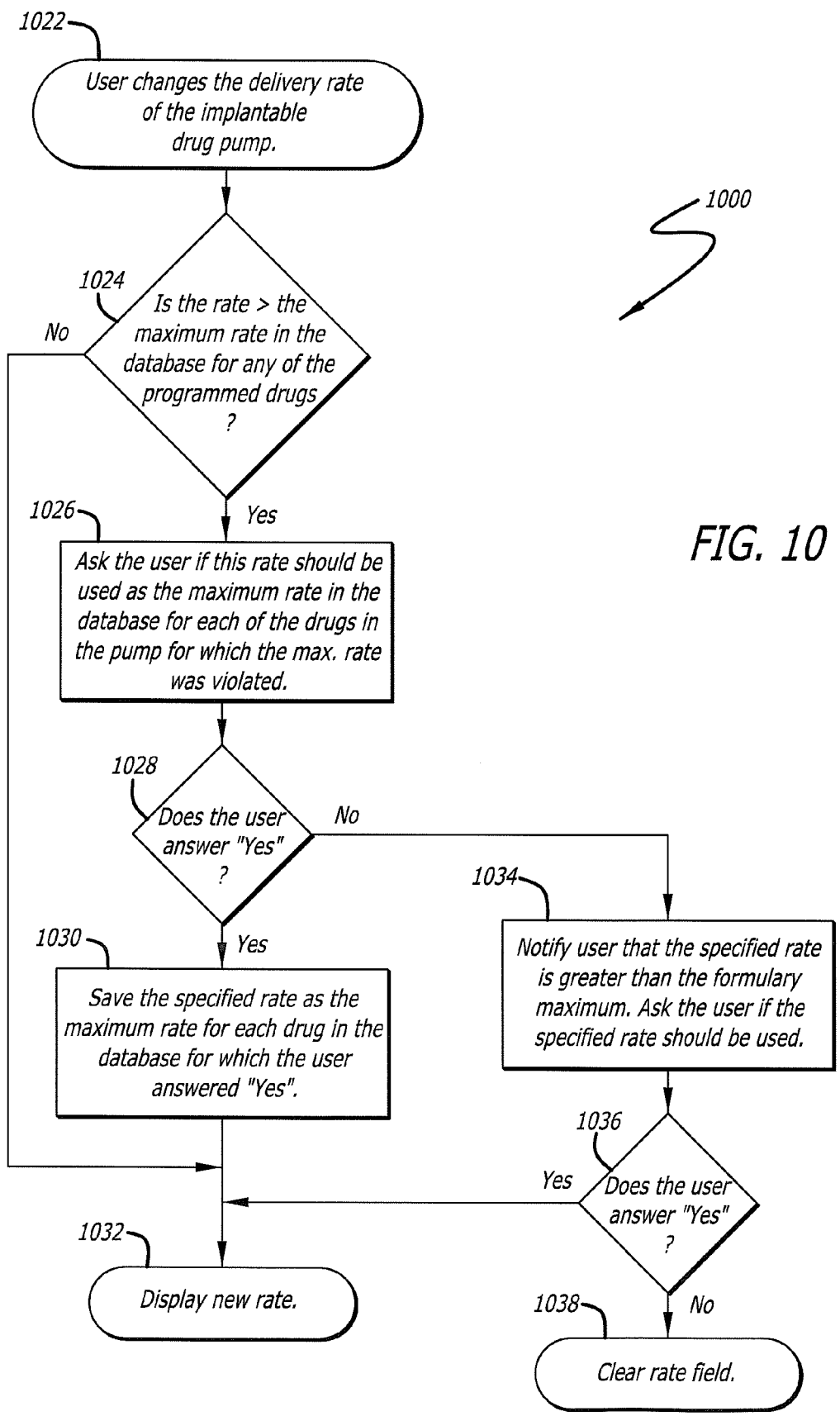
FIG. 10 is a flow chart in accordance with an embodiment of the present invention where a user changes the delivery rate of an implantable drug pump.

Referring to FIG. 10, in an example embodiment, a method 1000 of controlling a drug delivery safety system, in response to user changes to the delivery rate of an implantable drug pump, is now described. At 1022, a user changes the delivery rate for the implantable drug pump. A determination is made, at 1024, as to whether the rate is greater than the maximum rate in the database for any of the programmed drugs. If no, there is no need to adjust the maximum rate for each drug in the database and, at 1032, the new rate is displayed. If yes, at 1026, the user is prompted to indicate whether this rate should be used as the maximum rate in the database for each of the drugs in the pump for which the maximum rate was violated. At 1028, the user answer to this prompt is processed. If the user answer is "Yes", at 1030, the specified rate is saved as the maximum rate for each drug in the database for which the user answered "Yes". If the user answer is "No", at 1034, the user is notified that the specified rate is greater than the formulary maximum. Additionally, the user is asked to verify again that the specified rate should be used. At 1036, the user answer to this prompt is processed. If the user answer is "Yes", at 1032, the new rate is displayed. If the user answer is "No", at 1038, the rate field is cleared.

In an example embodiment, a drug delivery safety system includes a programmer with a display and a communications device adapted to communicate with an ambulatory medical device. The programmer has access to a database of information, and is adapted to receive and process the information and a user input and to control the display to provide a graphical user interface that prompts a user of the programmer to provide an additional user input when the user input requests a drug delivery protocol for the ambulatory medical device that is not already stored in the database as a clinician-approved drug delivery protocol. By way of example, the ambulatory medical device can be an implantable medical device or implantable drug pump. In an example embodiment, the information is clinic-specific and/or patient-specific.

In an example embodiment, the programmer is adapted to deny a requested drug delivery protocol that is not clinician-approved. In an example embodiment, the programmer is adapted to limit a requested drug delivery protocol, that is not clinician-approved, to conform with the clinician-approved drug delivery protocol.

In an example embodiment, the programmer is adapted to control the graphical user interface to prompt the user for a verification of a requested change to the drug delivery protocol. By way of example, the requested change can be one or more of: a therapeutic change, a concentration change, and a rate change.

In an example embodiment, the programmer is adapted to control the graphical user interface to prompt the user for a verification of a request to add a new drug delivery protocol to the database. In an example embodiment, the new drug delivery protocol is for a new drug that is not already associated with any clinician-approved drug delivery protocol stored in the database.

In an example embodiment, the programmer is adapted to control the graphical user interface to generate a warning to the user that the requested change to the drug delivery protocol is not clinician-approved. In an example embodiment, the warning is generated when the requested change exceeds a permitted change to a dosage for a particular drug. By way of example, the dosage is a daily dosage or a Patient Controlled Analgesia (PCA) dosage. By way of example, the permitted change is a (fixed) percentage increase or decrease (e.g., 20%). In an example embodiment, the warning is generated when the requested change exceeds a maximum rate limit for a particular drug. By way of example, the maximum rate limit can be either of maximum basal rate, a maximum temporary rate, or a maximum Patient Controlled Analgesia (PCA) bolus rate. The maximum temporary rate is a rate that displaces the maximum basil rate (e.g., during a particular time interval each day). In an example embodiment, the warning prompts the user to indicate whether the user wishes to override the warning. In an example embodiment, the warning prompts the user to indicate whether the user wishes to modify the clinician-approved drug delivery protocol. In an example embodiment, the warning prompts the user to indicate whether the user wishes to create a new drug delivery protocol.

In an example embodiment, the programmer is adapted to control the graphical user interface to generate a confirmation window relating to data that is to be written to the ambulatory medical device. In an example embodiment, the confirmation window displays both previous and new values for the drug delivery protocol. In an example embodiment, the confirmation window displays programming changes as highlighted. In an example embodiment, the confirmation window prompts the user to indicate whether the user wishes to accept programming changes before data is written to the ambulatory medical device.

Figure 7:
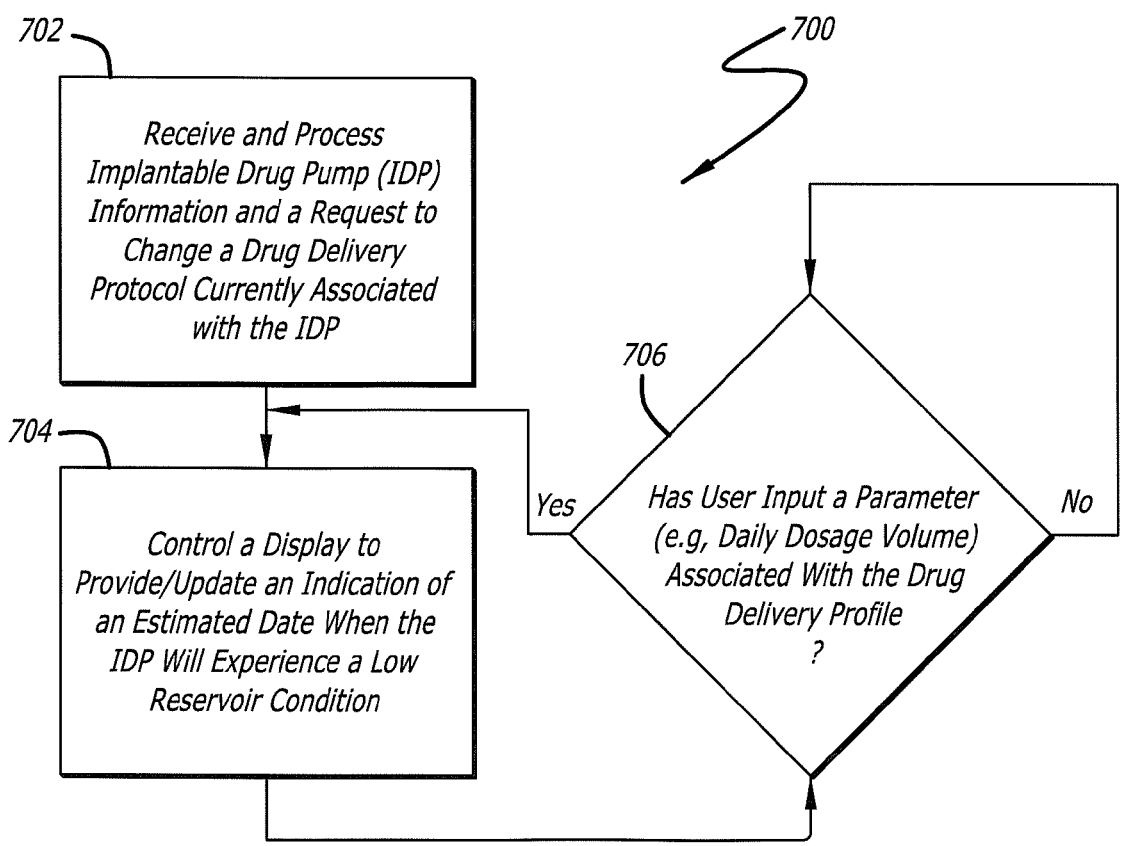
FIG. 7 is a flow chart in accordance with another embodiment of the present invention.

Referring to FIG. 7, in an example embodiment, a method 700 of controlling a drug delivery safety system is now described. At 702, implantable drug pump (IDP) information and a request to change a drug delivery protocol currently associated with the IDP are received and processed (e.g., by the controller 138). At 704, the display 148 is controlled to provide/update an indication of an estimated date when the IDP will experience a low reservoir condition. At 706, a determination is made as to whether a user has input a parameter (e.g., daily dosage volume) associated with the drug delivery profile. If "Yes", the controller processes the parameter and updates the indication of an estimated date when the IDP will experience a low reservoir condition. If "No", the processor monitors for new requests to change a drug delivery protocol currently associated with the IDP.

Figure 18:
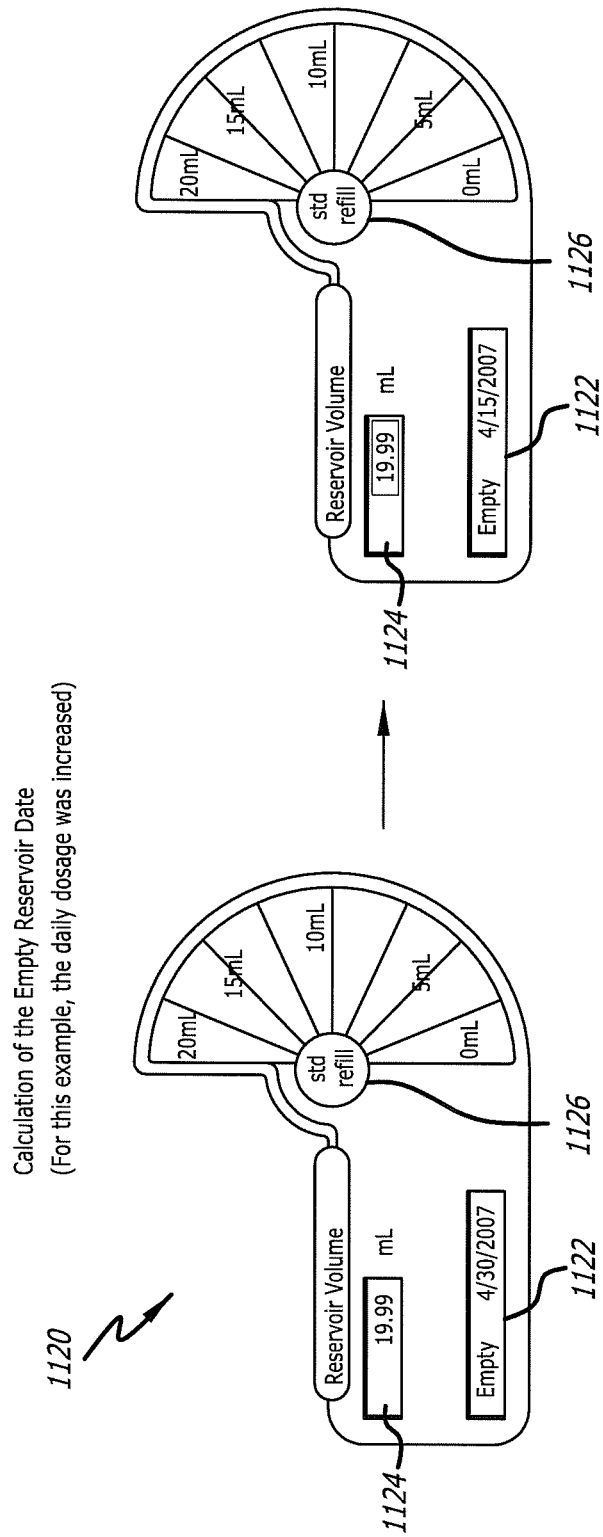
FIG. 18 shows a graphical user interface (displaying a calculation of an empty reservoir date in response to a daily dosage change) generated by a pump programmer according to an example embodiment of the present invention.

Referring again to FIG. 11, in this example embodiment, the graphical user interface 1100 includes a Reservoir Volume display area 1120, which displays a calculation of an empty reservoir date in response to a daily dosage change. Referring also to FIG. 18, in this example embodiment, the Reservoir Volume display area 1120 includes an empty reservoir date indication field 1122 which is updated by the controller 138 when a new value is entered into the daily dosage field 1124. In an example embodiment, the empty reservoir date is calculated based on the IDP's current delivery regime and any ongoing delivery procedures. In an example embodiment, the programmer 100a is configured such that the alarm 147 is activated on the empty reservoir date calculated. In this example embodiment, the Reservoir Volume display area 1120 includes a button 1126 which can be actuated by a user of the programmer 100a to request a standard refill for the implantable drug pump.

In an example embodiment, a drug delivery safety system includes a programmer with a display and a communications device adapted to communicate with an implantable drug pump. The programmer has access to a database of information relating to the implantable drug pump, and is adapted to receive and process the information and a user input relating to a requested change to a drug delivery protocol currently associated with the implantable drug pump, and to control the display to provide an indication of an estimated date in which the implantable drug pump will experience a low reservoir condition. By way of example, the requested change is to a daily dosage.

In an example embodiment, the programmer is adapted to control the display to generate a graphical user interface. In an example embodiment, the graphical user interface includes a field in which the indication of an estimated date is presented. In an example embodiment, the graphical user interface provides a graphical indication (e.g., a gage) of a reservoir volume for the implantable drug pump. In an example embodiment, the graphical user interface allows a user of the programmer to input a parameter associated with the drug delivery protocol. In an example embodiment, the programmer controls the graphical user interface to automatically update the indication of an estimated date depending upon the parameter. In an example embodiment, the parameter specifies a daily dosage volume. In an example embodiment, the graphical user interface includes a button which can be actuated by a user of the programmer to request a standard refill for the implantable drug pump.

Although the inventions disclosed herein have been described in terms of the preferred embodiments above, numerous modifications and/or additions to the above-described preferred embodiments would be readily apparent to one skilled in the art. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

What is claimed is:

1. A method of controlling a drug delivery safety system, said system having an implantable infusion pump configured to facilitate Patient Controlled Analgesia (PCA) and including a medication reservoir for holding one or more medications, and a programmer including a display and a communications device adapted to communicate with the implantable infusion pump, the method comprising:
    accessing at or via the programmer a database of information comprising a list of clinician-approved medications and associated clinician-approved drug delivery protocols; and
    utilizing the programmer to receive and process a user input and to control the display to provide a graphical user interface that prompts a user of the programmer to provide an additional user input when the user input requests a drug mixture containing at least one medication that is not already stored in the database as a clinician-approved medication.

2. The method of claim 1, further comprising:
    refilling the medication reservoir while the implantable infusion pump is within the patient.

3. The method of claim 1, further comprising:
    controlling the graphical user interface to display, in response to requests to refill the implantable infusion pump, a list of clinician-approved medications in the database of information for the implantable infusion pump and an option to use or specify a drug that is not on the list.

4. The method of claim 1, wherein the information is clinic-specific.

5. The method of claim 1, wherein the information is patient-specific.

6. The method of claim 1, further comprising:
    denying a requested drug delivery protocol that is not clinician-approved.

7. The method of claim 1, further comprising:
    limiting a requested drug delivery protocol that is not clinician-approved to conform with the clinician-approved drug delivery protocol.

8. The method of claim 1, further comprising:
    controlling the graphical user interface to prompt the user for a verification of a requested change to a drug delivery protocol.

9. The method of claim 8, wherein the requested change is a therapeutic change.

10. The method of claim 8, wherein the requested change is a concentration change.

11. The method of claim 8, wherein the requested change is a rate change.

12. The method of claim 1, further comprising:
    controlling the graphical user interface to prompt the user for a verification of a request to add a new drug delivery protocol to the database.

13. The method of claim 12, wherein the new drug delivery protocol is for a new drug that is not already associated with any clinician-approved drug delivery protocol stored in the database.

14. The method of claim 1, further comprising:
    controlling the graphical user interface to generate a warning to the user that the requested change to a drug delivery protocol is not clinician-approved.

15. The method of claim 14, wherein the warning is generated when the requested change exceeds a permitted change to a dosage for a particular drug.

16. The method of claim 15, wherein the dosage is a daily dosage.

17. The method of claim 15, wherein the dosage is a Patient Controlled Analgesia (PCA) dosage.

18. The method of claim 15, wherein the permitted change is a fixed percentage increase.

19. The method of claim 15, wherein the permitted change is a fixed percentage decrease.

20. The method of claim 15, wherein the permitted change is approximately 20%.

21. The method of claim 14, wherein the warning is generated when the requested change exceeds a maximum rate limit for a particular drug.

22. The method of claim 21, wherein the maximum rate limit is a maximum basal rate.

23. The method of claim 21, wherein the maximum rate limit is a maximum temporary rate.

24. The method of claim 21, wherein the maximum rate limit is a maximum Patient Controlled Analgesia (PCA) bolus rate.

25. The method of claim 14, wherein the warning prompts the user to indicate whether the user wishes to override the warning.

26. The method of claim 14, wherein the warning prompts the user to indicate whether the user wishes to modify the clinician-approved drug delivery protocol.

27. The method of claim 14, wherein the warning prompts the user to indicate whether the user wishes to create a new drug delivery protocol.

28. The method of claim 1, further comprising:
controlling the graphical user interface to generate a confirmation window relating to data that is to be written to the implantable infusion pump.

29. The method of claim 28, wherein the confirmation window displays both previous and new values for a drug delivery protocol.

30. The method of claim 28, wherein the confirmation window displays programming changes as highlighted.

31. The method of claim 28, wherein the confirmation window prompts the user to indicate whether the user wishes to accept programming changes before data is written to the implantable infusion pump.

32. A method of controlling a drug delivery safety system, said system having an implantable infusion pump containing a mixture of medications, the implantable infusion pump being configured to facilitate Patient Controlled Analgesia (PCA), and a programmer including a display and a communications device adapted to communicate with the implantable infusion pump, the method comprising:
accessing at or via the programmer a database of information comprising a list of clinician-approved medications and associated clinician-approved drug delivery protocols; and
utilizing the programmer to receive and process a user input and to control the display to provide a graphical user interface that prompts a user of the programmer to provide an additional user input when the user input requests a drug delivery protocol that is not already stored in the database as a clinician approved drug delivery protocol.

33. The method of claim 1, further comprising:
controlling the graphical user interface to indicate, in relation to an attempt to enable a Patient Controlled Analgesia (PCA) dosage, medication defined not to be suitable for PCA in a clinical formulary.

34. The method of claim claim 1, further comprising:
controlling the graphical user interface to indicate, in relation to an attempt to enable a Patient Controlled Analgesia (PCA) dosage, a requested PCA dosage which is not less than an allowed threshold percentage.

35. The method of claim 34, wherein the allowed threshold percentage is a percentage of a Base Dose.

36. The method of claim 34, wherein the graphical user interface includes a field which, when actuated, confirms a request by the user for a particular PCA dosage.

37. The method of claim 1, wherein the graphical user interface includes a field which when actuated verifies that PCA is allowed for the requested medication.

38. The method of claim 1, further comprising:
providing confirmation dialogs relating to requested PCA dosages.

39. The method of claim 1, further comprising:
preventing users of the s stem from enabling PCA when at least one of the medications in the drug mixture has been defined not to be suitable for PCA.

40. The method of claim 1, further comprising:
preventing users of the system from configuring a PCA Bolus rate which exceeds a threshold rate.

41. The method of claim 32, wherein the requested drug delivery protocol involves one or more of
exceeding the maximum daily dose for at least one drug in the drug mixture,
exceeding the maximum base rate at least one drug in the drug mixture, and
exceeding the maximum concentration for at least one drug in the drug mixture.

42. A method of controlling a drug delivery safety system, said system having an implantable infusion pump configured to facilitate Patient Controlled Analgesia (PCA) and including a medication reservoir for holding one or more medications, and a programmer including a display and a communications device adapted to communicate with the implantable infusion pump, the method comprising:
accessing at or via the programmer a database of information comprising a list of clinician-approved medications and associated drug delivery protocols; and
utilizing the programmer to receive and process a user input and to control the display to provide a warning or indication when the user input requests a refill of the medication reservoir with a drug mixture containing at least one medication that is not associated with a clinician-approved drug delivery protocol stored in the database.

* * * * *